United States Patent [19]

Cunanan

[11] Patent Number: 4,732,144
[45] Date of Patent: Mar. 22, 1988

[54] MULTI-SECTION EMERGENCY TRANSPORT NECK IMMOBILIZER

[76] Inventor: Oscar S. Cunanan, 102 Dunedin Ct., Cary, N.C. 27511

[21] Appl. No.: 940,911

[22] Filed: Dec. 10, 1986

[51] Int. Cl.$^4$ .............................................. A61F 5/01
[52] U.S. Cl. ....................................... 128/878; 128/75; 128/78
[58] Field of Search .............. 128/75, 78, 87 R, 87 B, 128/84 R, DIG. 20, DIG. 23, 84 C

[56] References Cited

U.S. PATENT DOCUMENTS

| | | | |
|---|---|---|---|
| 3,915,161 | 10/1975 | Shields | 128/75 |
| 4,194,501 | 3/1980 | Watt | 128/DIG. 20 X |
| 4,632,099 | 12/1986 | Mollo | 128/87 B |

Primary Examiner—Richard T. Stouffer
Attorney, Agent, or Firm—B. B. Olive

[57] ABSTRACT

An emergency transport neck immobilizing brace incorporates a frame structure adapted for mounting on the shoulders of a patient suspected of having a neck injury and securable to the body of the patient by straps. The brace frame mounts a head halter with a two-point strap suspension arrangement and a ratchet mechanism which can be pivoted out of operative position or into operative position for placing the patient's head in traction. Inflatable cushion devices limit forward, backward and lateral movement of the patient's head after being placed in traction and provide an air cushioned restraint. Front and rear headbands provide an alternative restraining method.

10 Claims, 10 Drawing Figures

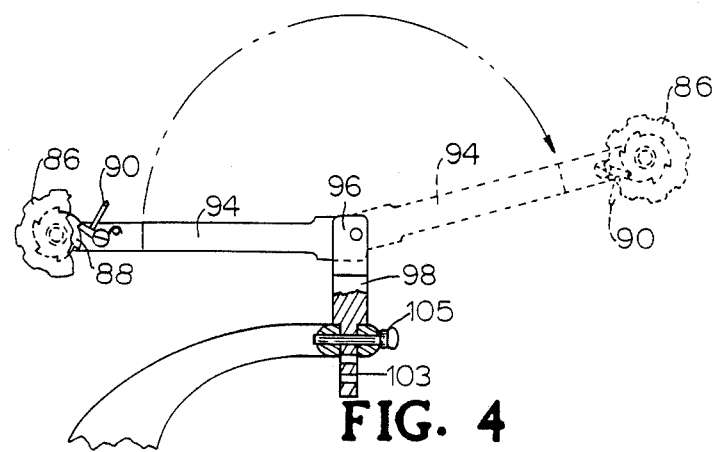
FIG. 4
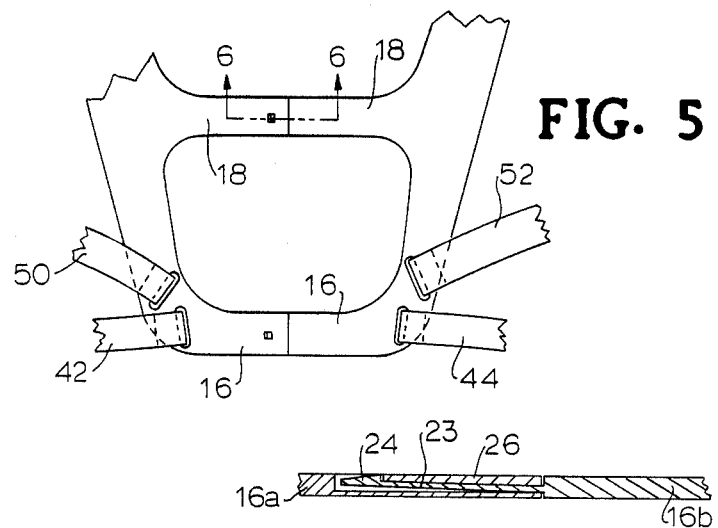
FIG. 5
FIG. 6

MULTI-SECTION EMERGENCY TRANSPORT NECK IMMOBILIZER

REFERENCE TO RELATED APPLICATION

This application is directed to an emergency brace improving on the emergency brace described in co-pending application Ser. No. 692,379, filed Jan. 17, 1985 entitled "Emergency Transport Neck Immobilizer" in which the present applicant is a co-inventor and issued as U.S. Pat. No. 4,632,099.

1. Technical Field

The invention relates broadly to braces for the human body and more specifically to an emergency and temporary brace for immobilizing a patient's neck.

2. Background Art

It has long been the practice in the medical art to brace the cervical spine of a person suspected of having or known to have a neck, cervical or spine injury. Often it is desirable to apply such a brace prior to moving the injured person from the scene of the accident. An emergency in-transient neck immobilizing brace, sand bags, board, or the like, applied at the scene of the accident is often and necessarily replaced by another brace, once the patient reaches the hospital and has gone through emergency examination and diagnostic procedures. In emergency use, certain basic characteristics are required for the brace which do not necessarily apply to the type of brace applied to the patient in the hospital environment. While various attempts have been made in the past to provide a neck brace particularly suited and intended solely for emergency transport and the initial emergency treatment and examination of a patient often including X-ray examination, no such brace has come into widespread use. What is believed to represent the closest prior art is fully noted in the co-pending application and will be set forth in U.S. Pat. No. 4,632,099 when issued.

The prior art related to body braces is otherwise voluminous. Therefore, only selected prior patents will be mentioned as being representative of approaches taken in the past. U.S. Pat. Nos. 2,642,864; 3,605,736; 3,795,243; 4,194,501 and 4,250,874 represent shoulder-supported braces with adjustable means for placing the head in traction. U.S. Pat. Nos. 3,507,273 and 4,161,946 represent other types of braces which rest on the body in a self-securing manner.

The brace set forth in co-pending application Ser. No. 692,379 comprised a unitary frame made up of radio transluscent, i.e., transluscent to x-ray, material. A pair laterally spaced, inverted U-shaped frame members constituting an upper frame were integrally joined at the bottom to another pair of inverted J-shaped members which constituted a lower frame and provided shoulder supports and back rest structure. Crotch straps and underarm straps were provided to secure the lower frame of the brace to the body. A fixedly positioned rotatable ratchet-operated bar on the upper frame suspended a pair of laterally spaced straps attached to a spring-loaded head halter which placed the head in traction. Forward and backward as well as lateral movement of the patient's head was limited by a pair of adjustable, curved cushions which partially surrounded and pressed against the sides of the head.

While the brace of co-pending application Ser. No. 692,379 is believed to have represented a substantial advance over the prior art, a disadvantage has been recognized in that the entire brace was required to be fitted over the body when applied. Additionally, the fact that the ratchet-operated bar could not be moved out of its fixed position or adjusted for the height of the patient also represented a disadvantage in certain emergency circumstances. Also recognized was a need for a frame structure in a more simplified form made up of two sections which could be snapped together at the scene of the accident. A need was also recognized for providing improved cushioning means for limiting the forward, backward and lateral movement of the patient's head without requiring excessive frame adjustment in order to minimize disturbing to the patient in pain at the scene of the accident. Finally, it has been found desirable in some situations to provide means for securing the head to the brace with headbands rather than cushions, e.g., for injuries to the side of the head.

With the prior art and the aforementioned disadvantages in mind, the present invention seeks to provide a further improved multi-section brace primarily intended for use during emergency transport of an individual suspected of having a neck injury, whether by air, sea or land emergency transport. Most specifically, the object of the invention is to provide such a brace with an improved multi-section frame, an improved pivotal and height adjustable ratchet mechanism for supporting the head halter, an improved cushioning means for limiting the forward, backward and lateral movement of the patient's head or alternatively a headband arrangement for a similar purpose. The achieving of these features is also intended to be achieved in an improved brace which does not interfere with the initial treatment through emergency care including possible X-ray and cardiology examinations. The foregoing and other objects will become apparent as the description proceeds.

BRIEF DESCRIPTION OF THE DRAWINGS

FIG. 4 is a partial side view of the ratchet bar support in a solid line operative position and in dash lines an inoperative position.

FIG. 5 is a partial front elevation view of the lower section of the frame indicating the strap connections and snap together features.

FIG. 6 is a partial cross section taken in the direction of line 5—5 of FIG. 5 illustrating a typical snap together construction employed at the snap together joints.

BEST MODE FOR CARRYING OUT THE INVENTION

Figure 1:
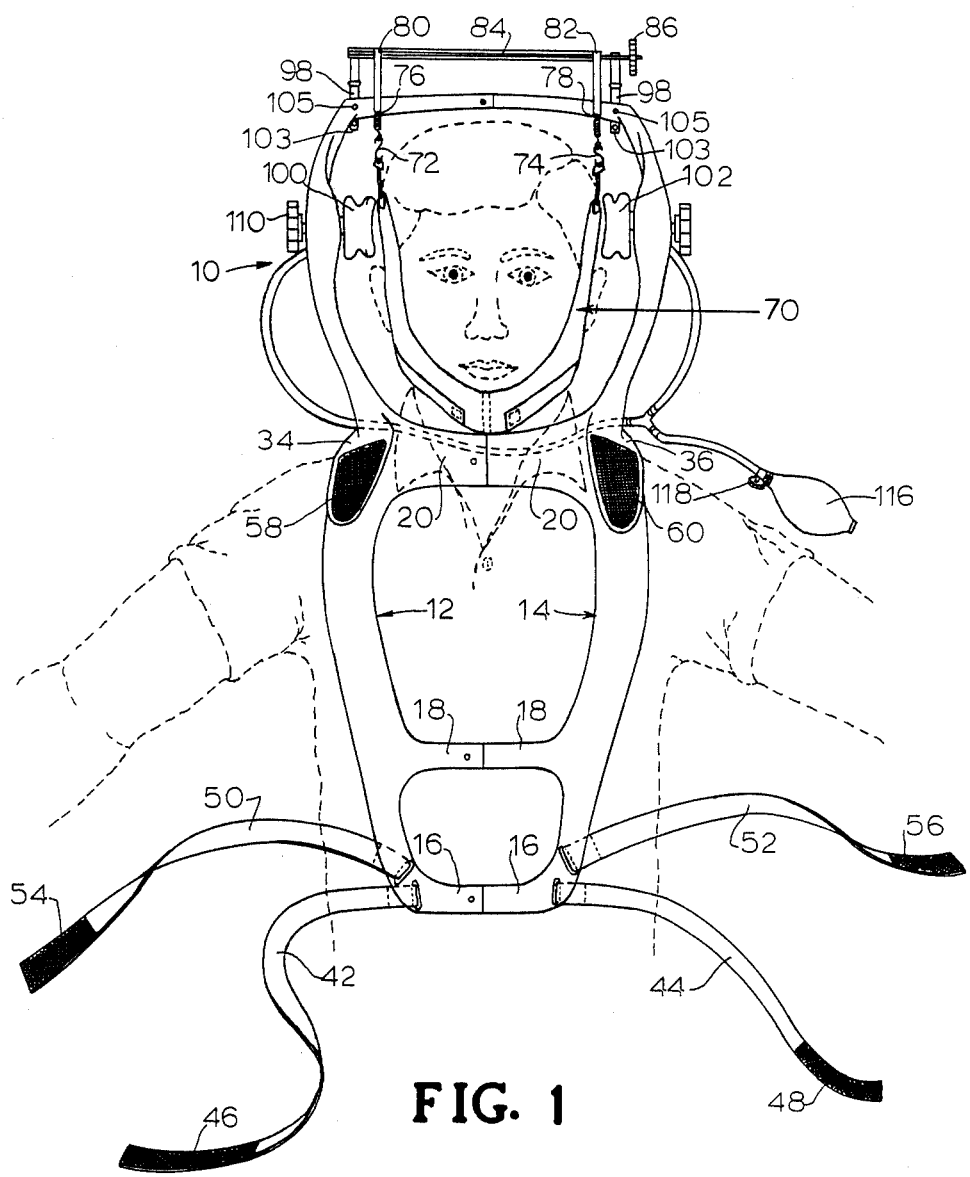
FIG. 1 is a front view of a patient indicated in dashed lines wearing an assembled brace according to the invention with the improved head cushions inflated, with the improved ratchet mechanism and head halter in place but with the body straps disconnected for purposes of illustration.

The brace 10 of the invention comprises a frame structure made up of two interconnected sections 12, 14 preferably formed of plastic, radiolucent material. The two frame sections 12, 14 are joined by a lower snap-together crossbar 16, middle snapped together crossbar 18 and top snap-together crossbar 20. Each of these crossbars utilize a plastic molded locking configuration such as illustrated in FIG. 6. Using the two sections of crossbar 16 as an example and designating such sections as 16a and 16b, section 16b is formed with a tongue 23, and push button like locking flange 24 designed to enter the slot 26 and lock when sections 16a and 16b are pressed together to form the integral lower crossbar 16 and to be depressed for unlocking. A similar construction is employed for each of the crossbars 16, 18 and 20. The two frame sections, 12 and 14 are further detachably connected together by the two halves of a somewhat U-shaped bar member 22 using a press lock construction such as in FIG. 6.

Figure 2:
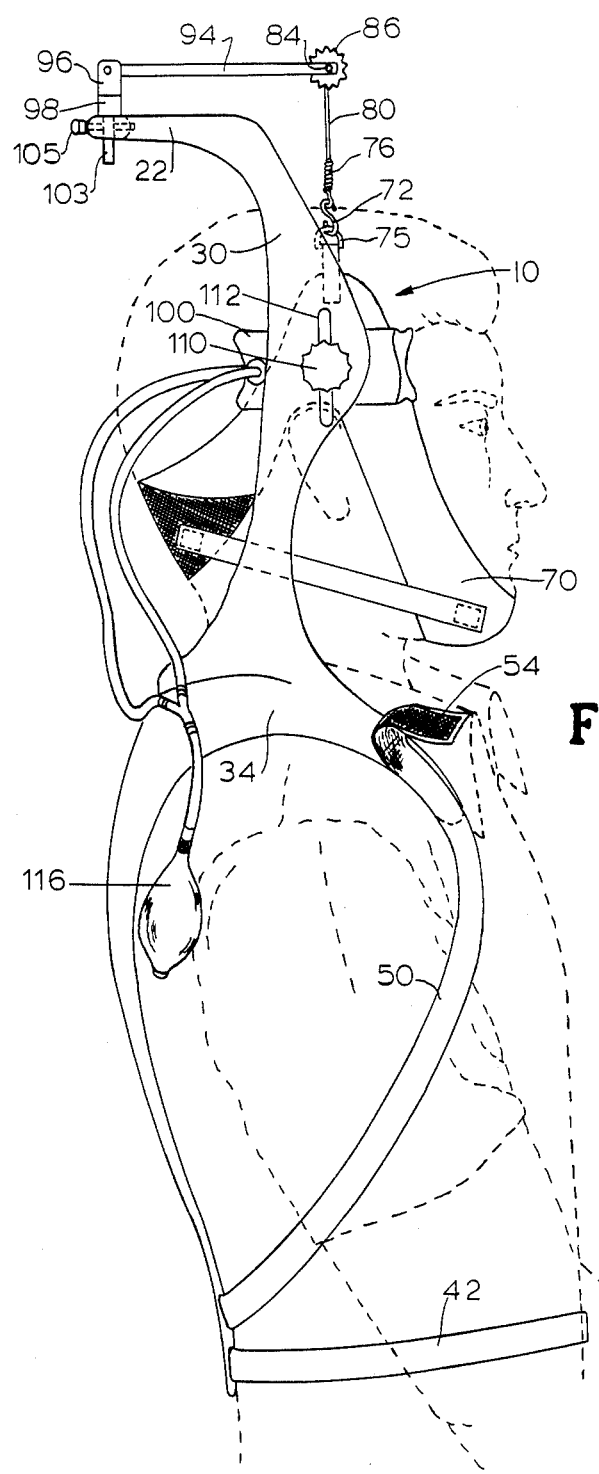
FIG. 2 is a side view of the patient wearing an assembled brace according to the invention and illustrating how the underarm and waist straps are secured.
Figure 3:
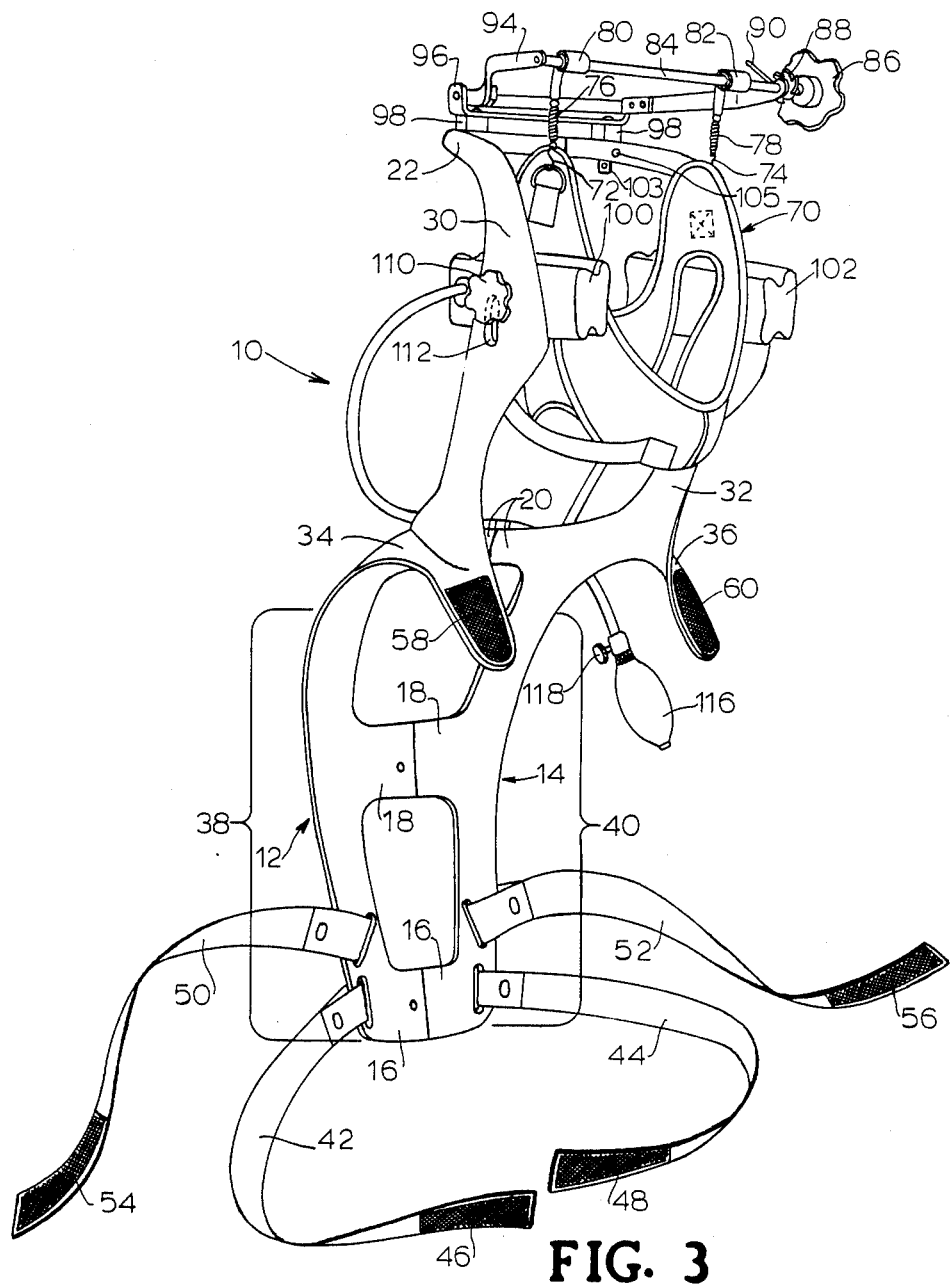
FIG. 3 is a front perspective view of the invention brace removed from the patient.

A pair of upwardly extending frame members, 30 and 32 are formed to reside on opposite sides of the patient's head, extend upwardly, and merge into the respective mated sections forming bar 22. Bar 22 with frame members 30, 32 form what is referred to as the upper immobilizing frame. A pair of opposed inverted J-shaped laterally spaced shoulder and body support members, 34 and 36 are integrally molded with frame members 30, 32 as well as with crossbars 16, 18 and 20. Support members 34, 36 with crossbars 16 and 18 form a lower body securing frame with the upper inverted U-shaped portions of sections 34, 36 being designed to rest on the patient's shoulders as indicated in FIGS. 1 and 2. The suitably curved back rest sections 38, 40 conform to the body and terminate with crossbar 16 preferably immediately above the location of the pelvic bone with crossbar 16.

Waist straps 42, 44 are preferably fitted with interengaging molded hook or Velcro type connectors 46, 48. A separate pair of straps 50, 52 fitted with mating hook and Velcro type fasteners 54, 56 mate with suitably formed hook or Velcro type fastening means 58, 60. Adjustment to size is of course achieved by selecting the desired location for connecting respective pairs of straps together.

A conventional head halter 70 is secured by snap hooks 72, 74, springs 76, 78 and laterally spaced straps 80, 82 to a rotatable bar 84 operated by handle 86 and use of a suitable ratchet mechanism 88 having a releasable pawl 90 (see FIG. 4). Ratchet bar 84 mounts in a pivotal frame 94. Frame 94 mounts on suitable pivots 96 supported on blocks 98 mounting height adjustable studs 103 with a series of holes detachably secured by suitable removable pins 105 to the respective sections 22a, 22b of bar 22. Thus, when the two frame sections 12, 14 are snapped together and pivotable frame 94 is suitably supported on bar 22, adjusted for the height of the patient and swung into the operative position as seen in FIG. 2, the head of the patient can be brought into traction in a 2-point suspension arrangement while allowing, through the provision of springs 76, 78 some mobility movement of the patient's chin. Springs 76, 78 also serve as some protection against overtightening of the ratchet mechanism 88.

In addition to providing means for placing the patient's head in traction, the invention brace 10 also, by means of the vertically, horizontally, and angularly adjustable, inflatable cushions 100, 102 provides means for comfortably, but securely limiting forward and backward, as well as lateral movement of the head of the patient, once the patient's head has been suitably tractioned by means of the previously described head halter mechanism.

Figure 7:
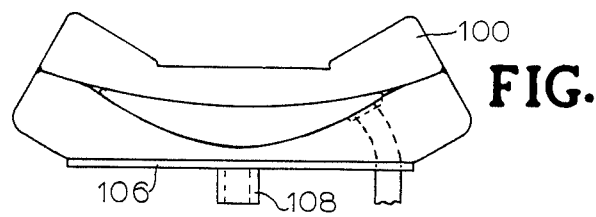
FIG. 7 is a plan view of an inflatable head cushion employed with the invention brace.
Figure 8:
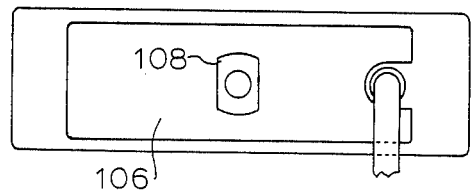
FIG. 8 is an elevation view of the inflatable head cushion.
Figure 9:
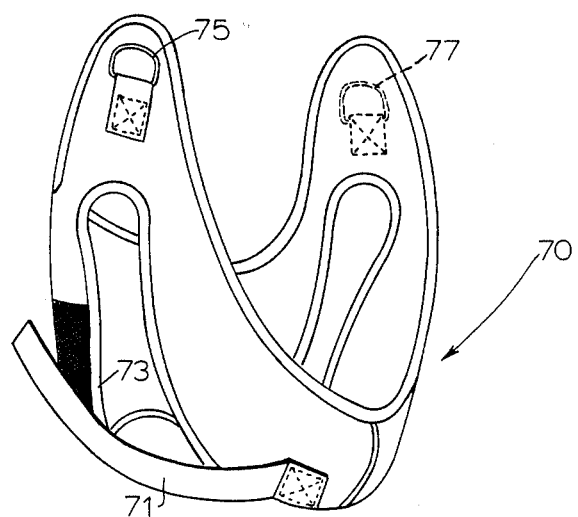
FIG. 9 is a perspective view of the head halter removed from the invention brace.

Cushions 100, 102 are of similar construction, with a representative construction being illustrated in FIGS. 7 and 8. As seen in FIGS. 7 and 8, inflatable cushion 100 mounts on a support plate 106, having an internally threaded screw receptacle 108, which receives a suitably threaded mating screw, not shown, extending from handle 110 through 112. The inflatable cushions 100, 102 are inflated by means of a pressure bulb 116, having a pressure release 118. Thus, it will be seen that vertical, horizontal and angular adjustments of cushions 100, 102 can be obtained, as well as some selected degree of pressure on the side of the patient's head, which can be regulated according to the accident conditions.

Brace 10 of the invention can be applied either by snapping the two frame sections 12, 14 together at the scene of the accident, or in appropriate circumstances can be applied as an assembled brace. When applied by snapping the two frame sections 12, 14 together, the ratchet mechanism is installed after the frame sections 12-14 have been assembled. Waist straps 42, 44 are fastened around the waist of the patient, when the respective straps 50, 52 are passed beneath the armpits of the patient and secured to the respective fastening means 58, 60. The ratchet mechanism is retracted backwards as in the dashed line position of FIG. 4, and adjusted for the height of the patient, following which the head halter 70 is applied over the head and approximated anteriorly over the chin, and fastened with a fastening strap 71 having mating hook or Velcro type connections 73. Head halter 70 is then secured by means of the connectors 75, 77 to the respective snap hooks 72, 74 connected to the respective straps 80, 82. The ratchet mechanism is then moved to the forward or operative position as seen in FIG. 2, and the head halter is then gently retracted upwards making sure that the respective springs 76, 78 are not overstretched. The inflatable cushions 100, 102 are next adjusted just above the ear on both sides, and locked into position with the respective screw handles 110, 111. The inflatable cushions 100, 102 are then inflated with the blood pressure type hand pump 116, sufficient to gently immobilize the head, and when necessary are additionally inflated to keep the head immobilized under the air cushion restraint.

Figure 10:
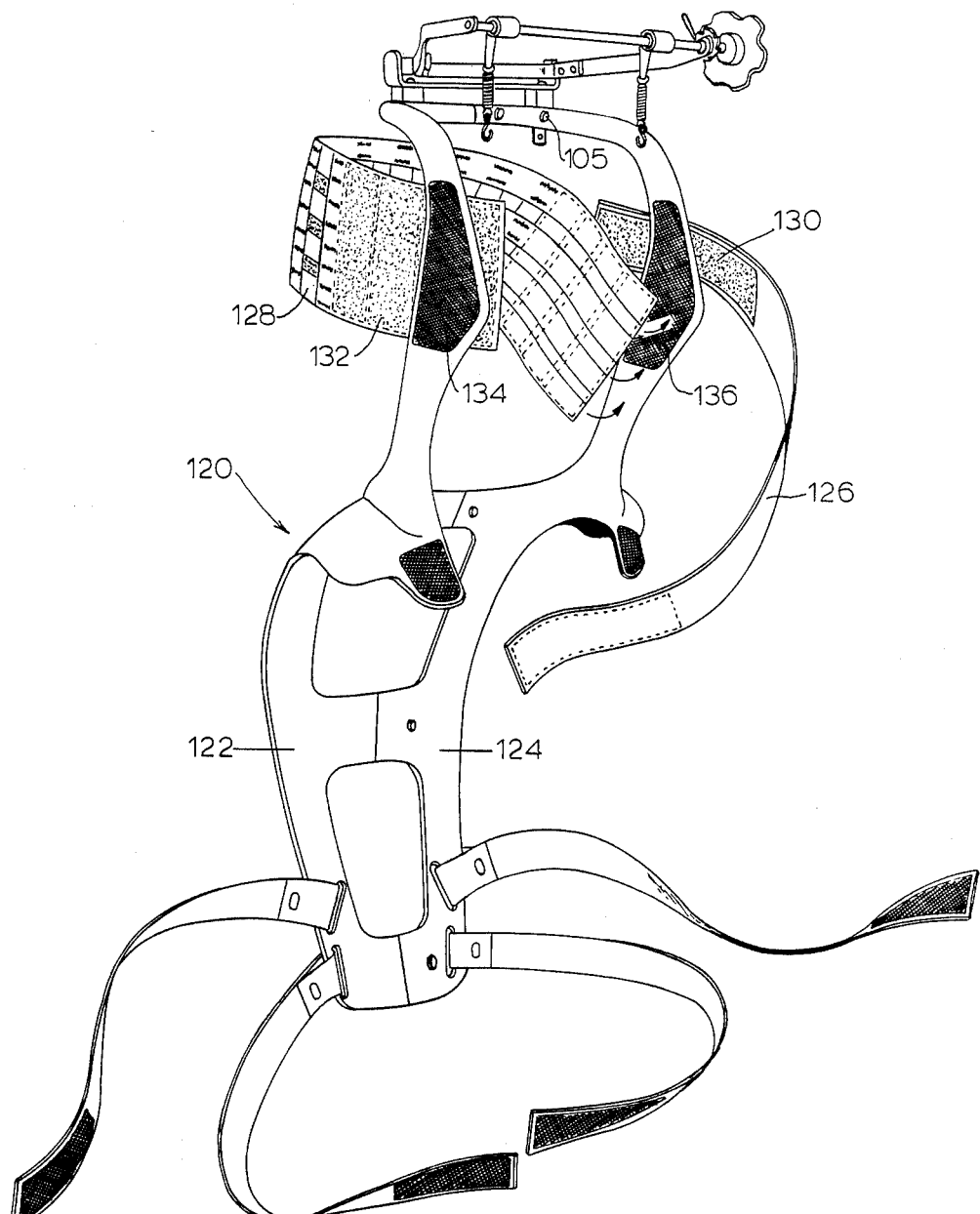
FIG. 10 is a perspective of an alternative brace arrangement using headbands in lieu of cushions to secure the head and with the head halter removed for purposes of illustration.

When removing the brace 10 from the patient, the ratchet mechanism is released to loosen the head halter 70, after which by use of the strap snap hooks 72, 74, halter 70 is removed. Cushions 100, 102 are deflated and head halter 70 is removed out of position by unstrapping the respective straps 71, 71. Straps 50, 52 are next released, followed by release of the waist straps 42, 44, after which the complete brace 10 is removed from the patient to complete its application. FIG. 10 illustrates an alternative embodiment for use in emergency situations such as in side head injuries of the like where the use of cushions 100, 102 is not desirable. For such situations the modified brace 120 made up of snap-together sections 122, 124 is fitted with a front headband 126 and a rear headband 128 with respective hook or Velcro-type fasteners 130, 132 mated to respective external hook or Velcro-type fasteners 136. The basic brace construction otherwise follows the construction previously explained. The invention brace from the foregoing description, offers at least these features and advantages:

(1) A ratchet mechanism which can be pivoted both out of position as well as into position for placing the patient's head in traction.

(2) An inflatable cushioned head securing means adapted to be positioned vertically and in an angular relation and to be inflated in some selected amount to establish a pre-selected lateral pressure on the head to accommodate various accident situations.

(3) A multi-section brace which when assembled can be secured to the body in a stable and comfortable manner solely by use of straps (4) A multi-section brace which can be installed on the patient either as an assembled brace or as two snapped together sections.

(5) A brace construction which leaves the chest area free for cardiac monitoring and cardiac examination.

(6) A brace which permits the patient's arms and legs, when not injured to remain mobile and unrestricted.

(7) A brace which does not have to be removed for preliminary examination in emergency room procedures but which can be easily removed both entirely or in sections in the emergency room when necessary with the patient in a supine position.

(8) A brace which imposes no respiratory or cardiac restriction, and permits ease of monitoring blood pressure particularly during emergency transport.

(9) A brace which when necessary can be used without the described cushions but instead with front and rear headbands.

What is claimed is:

1. An emergency transport neck immobilizing brace, comprising:
   (a) an integral rigid frame structure including:
      (i) a pair of laterally-spaced curved shoulder support frame portions formed to fit, be supported on, and be secured to the shoulders of a person's body;
      (ii) back frame portions extending from said shoulder support frame portions and forming open frame structure mountable behind and extending from the shoulders toward the pelvic region of said person's body; and
      (iii) support frame structure extending outwardly from said shoulder support frame portions opposite to the direction of extension of said back frame portions and including side frame structure formed to reside on opposite sides of and spaced outwardly from the head of said person's body;
      (iv) and a U-shaped frame member joined to said side frame structure at the extremity of said side frame structure opposite to said shoulder support frame portions, said U-shaped frame member extending generally perpendicular to and outwardly from said side frame structure a substantial distance rearwardly therefrom for providing a platform support proximate the rear of the head of said person's body for supporting a traction mechanism rearwardly of said side frame structure
   (b) strap and connector means on said frame structure providing straps of adjustable length and associated connectors mounted in a manner enabling said frame structure to be stably secured to the shoulders and other selected portions of said person's body with said shoulder support frame portions engaged with the shoulders of the person's body and said back frame portions engaged with the back of said person's body;
   (c) a head halter assembly mounted on said support frame structure and said U-shaped frame member including:
      (i) a chin-engaging head halter;
      (ii) a pair of laterally spaced straps secured to opposite sides of said halter; and
      (iii) a traction mechanism supported on rear portion of said U-shaped frame member rearwardly of said side frame structure and operatively associated with said pair of halter straps for placing in traction the head of the person's body employing said brace; and
   (d) a head-bracing assembly mounted on said side frame structure and adjustably engagable with opposite sides of the head of the person's body employing said brace in a manner effective to embrace opposite sides of the head for restraining lateral, forward and backward movement of the said person's head.

2. An emergency transport neck brace as claimed in claim 1 wherein said integral rigid frame structure is made up of two frame sections with means for detachably connecting said sections together at locations adapted to be substantially in alignment with the sagittal plane of a human body.

3. An emergency transport neck brace as claimed in claim 2 wherein said means for detachably connecting said sections together comprises mating snap fittings forming part of said frame sections at said locations.

4. An emergency neck brace as claimed in claim 2 wherein said head bracing assembly includes a pair of inflatable cushion means for being located to embrace opposite sides of the head only and means to inflate said cushion means in a manner to embrace said opposite sides of the head in air cushioned restraint.

5. An emergency transport neck brace as claimed in claim 1 wherein said mechanism includes a ratchet bar and ratchet apparatus mounted on a frame pivotal on said U-shaped frame member.

6. An emergency transport neck brace as claimed in claim 1 wherein said rigid frame structure is formed of radioluscent material.

7. An emergency transport neck brace as claimed in claim 1 wherein:
   (a) said integral rigid frame structure is made up of two frame sections with means for detachably connecting said sections together at locations adapted to be substantially in alignment with the sagittal plane of a human body;
   (b) said mechanism includes a ratchet bar and ratchet apparatus mounted on a frame pivotal on said U-shaped frame member; and
   (c) said rigid frame structure is formed of radioluscent material.

8. An emergency neck brace as claimed in claim 7 wherein said head bracing assembly includes a pair of inflatable cushion means for being located to embrace opposite sides of the head only and means to inflate said cushion means in a manner to embrace said opposite sides of the head in air cushioned restraint.

9. An emergency transport neck brace as claimed in claim 1 wherein said head bracing assembly includes a pair of inflatable cushion means for being located to embrace opposite sides of the head only and means to inflate said cushion menas in a manner to embrace said opposite sides of the head in air cushioned restraint.

10. An emergency transport neck brace as claimed in claim 1 wherein said head bracing assembly includes front and rear headbands detachable connected to said support frame structure.

* * * * *